United States Patent [19]

Hammond et al.

[11] 4,202,981
[45] May 13, 1980

[54] SUBSTITUTED -6,7,8,9-TETRAHYDRO-PYRIDO- AND 2H-PYRANO [2,3-B][1,8]NAPHTHYRIDINES, STABLE EFFICIENT LASER DYES

[75] Inventors: Peter R. Hammond, Livermore; Ronald A. Henry, China Lake; John A. Trias, La Mesa; Erhard J. Schimitischek, San Diego, all of Calif.

[73] Assignee: The United States of America as represented by the Secretary of the Navy, Washington, D.C.

[21] Appl. No.: 888,125

[22] Filed: Mar. 20, 1978

[51] Int. Cl.² .................. C07D 471/14; C07D 491/14
[52] U.S. Cl. ......................................... 546/82; 546/83
[58] Field of Search .................. 260/295 T; 546/82, 83

[56] References Cited
U.S. PATENT DOCUMENTS
3,891,569  6/1975  Schimitschek et al. .... 260/343.45 X OTHER PUBLICATIONS
Henry et al., J. Heterocyclic Chem., vol. 14 (Oct. 1977), pp. 1109–1114.

Neister, Optical Spectra, Feb. 1977, pp. 34–36.
Schimitschek et al., Optics Communications, vol. 16, No. 3 (1976), pp. 313–316.

*Primary Examiner*—Richard Raymond
*Attorney, Agent, or Firm*—R. S. Sciascia; W. Thom Skeer; L. E. K. Pohl

[57] ABSTRACT

Compounds having the formula:

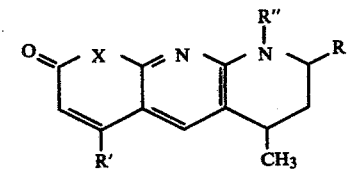

wherein X is selected from the group consisting of NH and O, R is selected from the group consisting of H, $CH_3$ and phenyl, R' is selected from the group consisting of $OCH_3$, $CF_3$ $CH_3$ and H and R" is selected from the group consisting of H, $CH_3$ and $CH_2CO_2$ $C_2H_5$. The compounds are stable, efficient laser dyes.

5 Claims, No Drawings

SUBSTITUTED -6,7,8,9-TETRAHYDRO-PYRIDO- AND 2H-PYRANO [2,3-B][1,8]NAPHTHYRIDINES, STABLE EFFICIENT LASER DYES

BACKGROUND OF THE INVENTION

1. Field of the Invention

This invention relates to heterocyclic compounds which emit laser light when properly stimulated.

2. Description of the Prior Art

In 1966 researchers first noted stimulated emissions from organic dye materials. Since that time, a wide array of organic dyes have been investigated and developed for use in what are now known as dye lasers, wherein an organic compound in solution replaces a gas or crystal (e.g. ruby) or the like as the active optical element. Laser dyes are so-called because they typically possess auxochromic groups such as oxygen and nitrogen and conjugated double bonds characteristic of classic organic dyes.

Laser dyes are economical, can be dissolved in optically clear solvents, and are not subject to cracks or other optical imperfections. The most interesting advantage of laser dyes, however, is their broadband emission. This permits the production of ultrashort pulses and the selection of output from one wavelength to another by simply "tuning" the laser to various wavelengths.

The broad family of laser dyes is classified for purposes of investigation into dyes of certain wavelength outputs: ultraviolet dyes, infrared dyes, etc. The present invention relates to blue-green laser dyes, which are of interest, for example, in underwater communications, as seawater is transmissive to light at about 480 nm wavelength.

Among the first laser dyes were the coumarins. Many of these dyes lase in the blue-green region but it was recognized very early that various substituents on and in the ring structure affect wavelength and output.

Chemical modifications of the basic coumarin structure also affect a dye's photostability. The tendency of laser dyes to break down after repeated optical stimulation is at present the greatest single drawback to the use of laser dyes. The problem is discussed by Schimitschek et al. in U.S. Pat. No. 3,891,569 and by Schimitschek et al. in "New Laser Dyes with Blue-Green Emission," 16 *Opt. Comm.* 313 (1976).

Ring substituents may have a dramatic effect on output and stability. The *Optics Communications* paper, supra, refers to two dyes, identified as AC1F and AC2F, which have a very similar ring structure, yet AC1F does not lase.

The inventors have found that AC2F, whose method of preparation has not heretofore been disclosed, is actually one of a family of stable, efficient blue-green lasing dyes.

SUMMARY OF THE INVENTION

According to this invention, stable, efficient laser dyes are prepared. They have the generic formula:

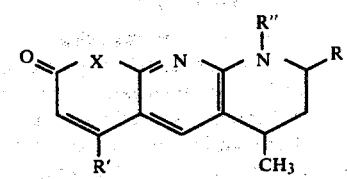

wherein R is selected from the group consisting of H, $CH_3$ and phenyl, R' is selected from the group consisting of $OCH_3$, $CF_3$, $CH_3$ and H, R" is selected from the group consisting of H, $CH_3$ and $CH_2CO_2C_2H_5$ and X is selected from the group consisting of O and NH.

Preparation of the compounds having the formula:

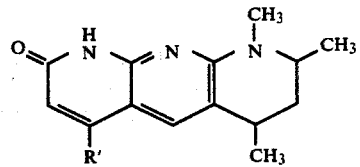

wherein R' is $CH_3$, OH or $CF_3$ is carried out by (a) condensing 2,6-diaminopyridine with 2,4-pentanedione to yield 7-amino-2,4-dimethyl-1,8-naphthyridine, (b) acetylating the naphthyridine to form the corresponding 7-acetamido naphthyridine, (c) methylating the 7-acetamido compound of step (b) to form a 1,2,4-trimethyl product, (d) hydrogenating the step (c) product to yield 7-acetamido-1,2,4-trimethyl-1,2,3,4-tetrahydro-1,8-naphthyridine, (e) hydrolyzing the product of step (d) under basic conditions and (f) condensing the product of step (e) with a β-diketone of the formula $R'COCH_2CO_2H_5$ wherein R' is $CH_3$, $CH_3$ or $OC_2H_5$.

To form a compound having the formula:

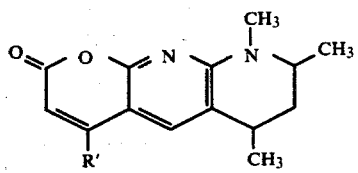

wherein R' is $CH_3$, OH or $CF_3$, the immediately proceeding series of steps is carried out with the exception that step (d) is carried out under basic rather than acidic conditions. The 1-methyl group may be replaced with hydrogen by selecting the appropriate starting compound. The 1-methyl group may be replaced with 1-carboethyoxymethylene by starting with the hydrogenated reaction product of ethyl bromoacetate and 7-acetamindo-2,4-dimethyl-1,8-naphthyridine.

DESCRIPTION OF THE PREFERRED EMBODIMENT

The preparation of the compounds of this invention is set forth below by means of a series of specific examples.

Example 1

7-Acetamido-2-chloro-4-methyl-1,8-naphthyridine

This compound was made from 7-acetamido-2-hydroxy-4-methyl-1,8-naphthyridine by the procedure described by Petrow, Rewald and Sturgeon in *J. Chem. Soc.* 1407 (1947).

Example 2

7-Acetamido-4-methyl-1,8-naphthyridine

The above chloro compound (11.8 g., 0.05 mole) was slurried with 200 ml of 3% potassium hydroxide in 95% ethanol, 2 g. of 5% palladium/calcium carbonate and 10–20 mg. of 10% palladium/carbon, and hydrogenated at 50 psi. After an induction period the pressure rapidly dropped 3.5–3.6 lb. The solution was filtered through Celite to remove the catalyst and the cake washed well with ethanol. The filtrate and washings were evaporated to dryness. The residue was slurried with 25 ml. of cold water, and the solid filtered, washed with two 10-ml. portions of water and dried; 5.8 g. (73%), m.p. 201°–204°, of 7-amino-4-methyl-1,8-naphthyridine. Ether extraction of the mother liquors plus washings yielded 0.62 g. (8%) more.

Recrystallization of 2.5 g. from 130 ml. of 9:1 benzeneethanol gave a mixture of golden needles and white crusts, both of which melted at 204.5°–205.5° and both of which had the same $^1$H nmr spectra. The ir spectrum of the golden needles suggested a hydrated form of 7-amino-4-methyl-1,8-naphthyridine (confirmed by analysis).

Anal. Calcd. for $C_9H_9N_3 \cdot 0.5H_2O$: C, 64.27; H, 5.99; N, 24.98. Found: C, 64.26; H, 5.97; N, 24.84.

Anal. on white crusts. Calcd. for $C_9H_9N_3$: C, 67.90; H, 5.70; N, 26.40; mol. wt. 159. Found: C, 67.94; H, 5.63; N, 26.43; mol. wt (mass spec.) 159.

The free 7-amino compound (12.0 g) was reconverted to the 7-acetamido by refluxing with 30 ml. of acetic anhydride for 1 hour. The cooled solution was slurried with 100 g. of ice plus 100 ml. of cold water, neutralized with sodium bicarbonate, warmed to dissolve all solids, then cooled overnight at 5°. The crystalline product was filtered, washed twice with cold water and dried; 13.3 g. (88%); m.p. 248°–251° dec. An additional 2.2 g. (m.p. 240°–250°) could be recovered by saturating the remaining aqueous phase with sodium chloride. When recrystallized from acetonitrile, the compound melted at 252°–253° dec.

Anal. Calcd. for $C_{11}H_{11}N_3O$: C, 65.65; H, 5.51; N, 20.88. Found: C, 65.49; H, 5.51; N, 20.72.

A small quantity of a diacetylated product, m.p. 145.5°–146.5°, after recrystallization from benzene-n-hexane, was isolated from one experiment.

Anal. Calcd. for $C_{13}H_{13}N_3O_2$: C, 64.18; H, 5.39; N, 17.27. Found: C, 64.16; H, 5.45; N, 17.32.

Example 3

7-Acetamido-1,4-dimethyl-1,8-naphthyridinium p-Toluenesulfonate

7-Acetamido-4-methyl-1,8-naphthyridine (13.3 g., 0.066 mole) was refluxed for 8 hours with 12.7 g. of methyl p-toluenesulfonate in 150 ml. of dry acetonitrile. The dark purple solution was cooled at 5° for several days; 21.8 g. (85%) of felted needles, m.p. 200°–202°, was removed. Addition of a large volume of ether to the mother liquors precipitated 2.3 g. (9%) more of the salt; m.p. 185°–190°. The $^1$H nmr was consistent with that expected for the desired product.

Example 4

7-Acetamido-1,4-dimethyl-1,2,3,4-tetrahydro-1,8-naphthyridine

The previous salt (11.6 g., 0.03 mole) was hydrogenated over 0.15 g. of platinum oxide in 100 ml. of glacial acetic acid containing 12 g. of ammonium acetate. Hydrogen uptake essentially ceased after the pressure dropped from 50 to 40 psi after 4 hours; the purple solution became colorless. The catalyst was removed, washed once with 20 ml. of acetic acid and twice with 20 ml. of water. The combined solutions were reduced to dryness on a rotary evaporator. The residue was dissolved in 100 ml. of water, cooled to 5°, made basic and ether extracted (2–100 ml.); the latter extracts, after washing once with a small volume of water, were dried over potassium carbonate. Evaporation left 5.34 g. (81%) of off-white solid, melting sharply at 95°–96°; $^1$H nmr (60 MHz, deuteriochloroform): δ1.20 (d,3H,$CH_3CH$—,J=7 Hz), 1.5–2.0 (m, 2H, $H_3$, $H_3$), 2.04 (s,3H,$CH_3CO$), 2.6–3.0 (m, 1H, $CH_3CH$—), 3.03 (s,3H,N—$CH_3$), 3.32 (t,2H,$H_2,H_2$,J=6 Hz), 7.22 (broad s, 2H, $H_5$, $H_6$), 8.08 (broad s, 1H, —NH—).

Example 5

7-Amino-1,4-dimethyl-1,2,3,4-tetrahydro-1,8-naphthyridine(1)

7-Acetamido-1,4-dimethyl-1,2,3,4-tetrahydro-1,8-naphthyridine (3.6 g.) in 50 ml. of 5% potassium hydroxide in 95% ethanol was refluxed for 8 hours under nitrogen. The solvent was then removed on a rotary evaporator and the residue slurried with 30 ml. of water. After cooling to 5° the solid product was removed, washed three times with cold water and dried, 2.82 g. (97%), m.p. 51°–53°. The amide carbonyl absorption had disappeared completely from the ir spectrum, which was also different from that the for 7-hydroxy compound obtained by acid hydrolysis of the amide. Recrystallization from n-hexane (0.5 g./10 ml.) by cooling to −15° furnished coarse, white grains, m.p. 52.5°–53.5°; $^1$H nmr (deuteriochloroform): δ1.17 (d, 3H, —CH—$CH_3$, J=7 Hz), 1.69 (m, 2H, $H_3$, $H_3$), 2.72 (m. 1H, $H_4$), 3.05 (s, 3H, $NCH_3$), 3.27 (t, 2H, $H_2,H_2$), 4.10 (broad s, 2H, $NH_2$), 5.72 (d, 1H, $H_6$, J=8 Hz), 7.02 (d,1H, $H_5$, J=8 Hz); fl. max (ethanol): 373 nm (exc. 325 nm); fl. max ($10^{-3}$ N perchloric acid in methanol): 416 nm (exc. 350 nm).

Anal. Calcd. for $C_{10}H_{15}N_3$: C, 67.76; H, 8.53; N, 23.71. Found: C, 68.19; H,3.38; N, 23.36.

Example 6

7-Hydroxy-1,4-dimethyl-1,2,3,4-tetrahydro-1,8-naphthyridine

7-Acetamido-1,4-dimethyl-1,2,3,4-tetrahydro-1,8-naphthyridine (1.27 g.) was dissolved in 16 ml. of 6 N hydrochloric acid, allowed to stand 3 days at 25°, then heated in the steam bath for 5 hours. The solution was cooled in an ice bath, made basic and the oily product which separated extracted into ether (some ether insoluble solid was removed by filtration). Evaporation of the dried ethereal solution left 0.38 g (37%) of a solid melting at 134°–136°. Golden plates, m.p. 134°–135°, were obtained by recrystallization from cyclohexane. The $^1$H nmr spectrum is consistent with the assigned structure.

Anal. Calcd. for $C_{10}H_{14}N_2O$: C, 67.38; H, 7.92; N, 15.72; mol. wt. 178.2. Found: C, 67.36; H, 8.02; N, 15.61; mol. wt. (mass spec.) 178.

Example 7

7-Amino-2,4-dimethyl-1,8-naphthyridine

2,6-Diaminopyridine (43.6 g., 0.4 mole), 40.0 g (0.4 mole) of 2,4-pentanedione, 200 ml. of glacial acetic acid and 5 ml. of 96% sulfuric acid were mixed, then refluxed with stirring for 24 hours. The cold solution was added slowly with good stirring and ice bath cooling to 160 g of sodium hydroxide in enough water to make 600 ml. The brown solid, which crystallized, was filtered after the solution had been cooled overnight at 5°, washed twice with cold water and dried, 25.3 g., m.p. 125°–200°. This crude material was dissolved in 130 ml. of boiling 95% ethanol and the solution chilled overnight at −15°, 19.5 g. (28%), m.p. 215°–220°. This material was suitable for the following experiment.

Example 8

7-Acetamido-1,2,4-trimethyl-1,2,3,4-tetrahydro-1,8-naphthyridine

This compound was made in 72% yield from the previous material using the same sequence of reactions described above for the corresponding dimethyl derivative; acetylation, methylation, and hydrogenation. The white, felted needles after recrystallization from cyclohexane melted 152.5°–153.5°.

Anal. Calcd. for $C_{13}H_{19}N_3O$: C, 66.92; H, 8.21; N, 18.01. Found: C, 67.03; H, 8.52; N, 17.84.

Example 9

7-Hydroxy-,1,2,4-trimethyl-1,2,3,4-tetrahydro-1,8-naphthyridine (2)

The previous compound (3.2 g.) was heated for 18 hours on the steam bath with 40 ml. of 6 N hydrochloric acid. The cooled solution was neutralized with 25% aqueous sodium hydroxide; the orange oil which separated soon crystallized. It was removed, washed with water and dried; 2.66 g. (100%), m.p. 143°–145°. Recrystallization from 8:2 cyclohexane-benzene, with carbon decolorization gave white grains, m.p. 146°–148°.

Anal Calcd. for $C_{11}H_{16}N_2O$: C, 68.71; H, 8.39; N, 14.57. Found: C, 68.20; H, 8.67; N, 14.52.

Example 10

7-Amino-1,2,4-trimethyl-1,2,3,4-tetrahydro-1,8-naphthyridine

The viscous oil recovered from the alkaline hydrolysis of the corresponding 7-acetamido compound was used without further purification.

Example 11

2-Oxo-6,9-dimethyl-4-trifluoromethyl-6,7,8,9-tetrahydro-2H-pyrano [2,3-b][1,8]naphthyridine The following procedure is typical of that used to prepare the various azacoumarins. 7-Hydroxy-1,4-dimethyl-1,2,3,4-tetrahydro-1,8-naphthyridine (0.19 g.), 1.2 ml. of ethyl trifluoroacetoacetate, 50 mg. of anhydrous zinc chloride, and 10 ml. of absolute ethanol were refluxed for 40 hours. The cooled solution was poured with stirring into 50 ml. of water plus 3 ml. of hydrochloric acid; the yellow precipitate was filtered, washed with water, and dried (0.31 g., 95%). Solvent used for recrystallization, melting point, fluorescence data and analytical data are summarized in the table below. The $^1H$ nmr spectral data (deuteriochloroform, 100 MHz) on the analogous 6,8,9-trimethyl derivative are: δ1.37 (d, 6H, CH₃CH), 1.47 (m,1H, H₇ᵦ), 2.10 (dt, 1H, H₇ₐ,J=13 Hz, J=4 Hz), 2.80 (m, 1H, H₆), 3.20 (s, 3H, NCH₃), 3.70 (m, 1H, H₈), 6.38 (s, 1H, H₃), 7.41 (q, 1H, H₅, $J_{H_5}$ —CF₃= ~1.5 Hz).

Example 12

2-Oxo-6,9-dimethyl-4-trifluoromethyl-1,2,6,7,8,9-hexahydropyrido[2,3-b][1,8]naphthyridine This is a representative procedure for making azaquinolones. 7-Amino-1,4-dimethyl-1,2,3,4-tetrahydro-1,8-naphthyridine (0.9 g.) and 1.0 g. of ethyl trifluoroacetoacetate were heated at 145°–165° for 18 hours. The cooled, semisolid mass was slurried with 5 ml. of ether, filtered and washed with more ether, 1.3 g., m.p. 225°–230°, wet 200°. Other data are found in the table. $^1H$ nmr (deuteriochloroform, 100 MHz): δ1.30 (d,3H, CH₃CH, J=7 Hz), 1.74 (m, 1H, H₇ₐ or H₇ᵦ), 1.89 (m, H, H₇ₐ or H₇ᵦ), 2.92 (m, 1H, H₆), 3.20 (s, 3H, NCH₃), 3.49 (t, 2H, H₈, H₈, J=6 Hz), 6.62 (s, 1H, H₃), 7.46 (q, 1H, H₅, $^JH_5$—CF₃= ~1.5 Hz), 9.40 (broad s, 1H,NH).

Example 13

7-Amino-4-methyl-2-phenyl-1,8-naphthyridine 2,6-Diaminopyridine (16.4 g., 0.15 mole), 24 g. of benzoylacetone, 75 ml. of acetic acid and 1.5 ml of 96% sulfuric acid was refluxed with stirring for 24 hours. The solution was poured slowly with stirring into 50 g. of sodium hydroxide in 250 ml. of water; the temperature was held 20°–30° by cooling. The tan solid was filtered, washed well with water and dried, 21.8 g. One recrystallization from 100 ml. of 95% ethanol gave 6.9 g. of coarse needles, m.p. 65°–190°; a second recrystallization from 50 ml. of ethanol furnished 2.1 g. (6) of the title compound, m.p. 253°–255°; $^1H$ nmr (deuteriochloroform+DMSO-d₆, 60 MHz): δ2.67 (s,3H, CH₃), 6.20 (broad exchangeable s, 2H, NH₂), 6.92 (d, 1H, H₅, J=9 Hz), 7.58 (d,1H, H₆), 7.50 (m,3H,meta and para protons on C₆H₅), 8.30 (m,2H, ortho protons on C₆H₅).

Anal. Calcd. for $C_{15}H_{13}N_3$: C,76.57; H, 5.57; N, 17.86. Found: C, 76.99; H, 5.62; N, 17.96.

From the aqueous mother liquors from which the above compound has been isolated there was recovered upon cooling 6.3 g. of an off-white solid. Recrystallization from water gave felted, white needles, melting in part 190°–192°, the balance 205°–207°. The $^1H$ nmr suggested a mixture of tautomeric and/or isomeric diacetyldiaminopyridines.

Anal. Calcd. for $C_9H_{11}N_3O_2$: N, 21.76. Found: N, 21.54.

Example 14

2-Oxo-6,9-dimethyl-8-phenyl-4-trifluoromethyl-6,7,8,9-tetrahydro-2H-pyrano[2,3-b][1,8]naphthyridine 7-Amino-4-methyl-2-phenyl-1,8-naphthyridine (2.0 g.) was mixed with 4 ml. of acetic anhydride; the solution was allowed to stand 1 hour at 25°, refluxed for 3 hours, cooled, and diluted with 15 ml. of water. After the excess anhydride hydrolyzed, the solution was made slightly basic with 25% aqueous sodium hydroxide (cooling used). The precipitated solid was filtered, washed well with cold water and dried, 2.3 g. (98%), m.p. 209.5°–210.5° after partial melting and resolidification at 150°–160°.

All of the above amide was refluxed for 8 hours in 25 ml. of dry acetonitrile with 1.6 g. of methyl p-toluenesulfonate. Cooling and addition of a large excess of ether yielded 3.34 g. (88.5%) of a blue-purple solid. The salt in 25 ml. of acetic acid containing 3 g. of ammonium acetate was hydrogenated over 0.1 g. of platinum oxide at an initial pressure of 50 psi; the theoretical amount (2 mole equivalents) was rapidly absorbed. The catalyst was removed, washed with 3 ml. of acetic acid, and two 10-ml. portions of water: the combined filtrates were evaporated to thick syrup which was then dissolved in 75 ml. of 65% ethanol and made basic with 25% aqueous sodium hydroxide. Water (75 ml.) was added to precipitate the product which was filtered off after overnight cooling at 5°. After washing with cold water, the wet, crude 7-acetamido-1,4-dimethyl-2-phenyl-1,2,3,4-tetrahydro-1,8-naphthyridine was heated overnight on the steam bath with 30 ml. of 6 N hydrochloric acid. Cooling, followed by careful neutralization with sodium hydroxide solution, furnished 1.2 g. of the 7-hydroxy derivative. The latter (a pale orange powder) melted at 211°–213° after one recrystallization from 60 ml. of 95:5 benzene-ethanol; $^1$H nmr (deuteriochloroform, 60 MHz); $\delta$1:30 (d, 3H, CH$_3$CH, J=6.5 Hz), 1.6–2.6 (m, 3H, H$_3$, H$_3$, H$_4$), 3.10 (s, 3H, NCH$_3$), 4.72 (dd, 1H, H$_2$, J=4 Hz, J=10 Hz), 6.19 (d, 1H, H$_5$, J=9.5 Hz), 7.43 (s, 5H, C$_6$H$_5$), 7.60 (d, 1H, H$_6$, J=9.5 Hz), 12.1 (broad s, 1H, OH, or NH).

A solution consisting of 0.7 g. of the 7-hydroxy-1,4-dimethyl-2-phenyl-1,2,3,4-tetrahydro-1,8-naphthyridine, 3 ml. of ethyl trifluoroacetoacetate, 20 ml. of absolute ethanol and 0.47 g. of anhydrous zinc chloride was refluxed for 64 hours. After cooling, the solution was diluted with 20 ml. of water plus 1 ml. of concentrated hydrochloric acid. The yellow solid which precipitated was filtered, washed with water and dried, 0.24 g. (23%). Other data can be found in the table below. The position of the phenyl group in this compound was assigned on the basis of the analysis of the $^1$H nmr spectrum of its precursor and of the following sulfonated derivative.

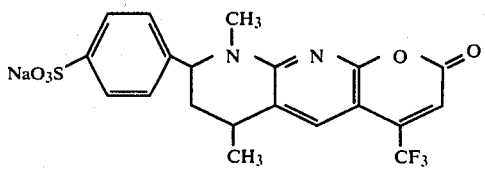

The previous compound was sulfonated with 20% oleum (15°–20°, 4 hours). After quenching on ice, neutralizing with sodium bicarbonate and evaporating the solution to dryness, the sulfonate was extracted with boiling 95% ethanol. The product crystalllized from the cooled extracts upon the addition of diethyl ether (40 ethanol-30 ether); fl. max (water): 473 nm (exc. 390 nm). The phenyl group was assigned to the 8-position rather than the 6-position based on the following $^1$H nmr evidence: the downfield methine proton again appeared as a quartet (splitting by the H$_7$ axial and H$_7$ equatorial protons) rather than a very complex multiplet one would expect if a methyl group were in the 8-position.

Anal. Calcd. for C$_{20}$H$_{16}$F$_3$N$_2$O$_5$SNA $\cdot$ 2.5H$_2$O: F, 10.93; N, 5.37; S, 6.15. Found: F, 10.96; N, 5.27; S, 6.18.

Example 15

7-Acetamido-1-carboethoxymethylene-2,4-dimethyl-1,2,3,4-tetrahydro-1,8-napthyridine The reaction product (9.4 g.) of ethyl bromoacetate and 7-acetamido-2,4-dimethyl-1,8-naphthyridine was hydrogenated by the same procedure used for the anlogous methyl compounds. Work-up in a similar manner gave 5.3 g. (71%) of crude product, m.p. 100°–104°. One recrystallization from n-hexane gave pale yellow blades, m.p. 110°–111°.

Anal. Calcd. for C$_{16}$H$_{23}$N$_3$O$_3$: C, 62.93; H, 7.59; N, 13.76. Found: C, 62.94; H, 7.57; N, 13.69.

The crude 7-hydroxy compound obtained by acid hydrolysis was used for the preparation of the azacoumarin without purification.

The correlation between fluorescence and lasing behavior is well known. The following table summarizes fluorescent and other physical properties of the dyes of the present invention according to substituents in the generic formula above.

Table

Substituted 1,2-Dihydropyrido- and 2H-Pyrano[2,3-b][1,8]naphthyridines

| X | R' | R | R'' | Empirical formula | Yield[a] % | M.p., °C. | Recrystallization solvent | Fluorescence max in ethanol (Excited, nm) | C,% (Theory) | H,% (Theory) | N,% (Theory) | F,% (Theory) |
|---|----|---|-----|-------------------|------------|-----------|---------------------------|-------------------------------------------|--------------|--------------|--------------|--------------|
| O | H[b] | CH$_3$ | CH$_3$ | C$_{14}$H$_{16}$N$_2$O$_2$ | 30 | 111–112 | 1:1 C$_6$H$_6$—C$_6$H$_{12}$ | 437(375) | 69.06(68.82) | 6.57(6.60) | 11.08(11.47) | — |
| O | CH$_3$ | CH$_3$ | CH$_3$ | C$_{15}$H$_{18}$N$_2$O$_2$ | 11 | 189–190 | 50% ethanol | 430(375) | 69.95(69.74) | 6.39(7.02) | 10.79(10.80) | — |
| O | CF$_3$ | H | CH$_3$ | C$_{14}$H$_{13}$F$_3$N$_2$O$_2$ | 95 | 163.5–154.5 | 65% ethanol | 482(400) | 56.2 (56.37) | 4.33(4.39) | 9.36(9.39) | 19.35(19.11) |
| O | CF$_3$ | CH$_3$ | H | C$_{14}$H$_{12}$F$_3$N$_2$O$_2$ | —[c] | 210–212 | 95% ethanol | 473(395) | 56.05(56.37) | 4.51(4.39) | 9.22(9.39) | — |
| O | CF$_3$ | CH$_3$ | CH$_3$ | C$_{15}$H$_{15}$F$_3$N$_2$O$_2$ | 91 | 167–168 | 75% ethanol | 480(394) | 57.91(57.69) | 5.00(4.84) | 8.77(8.97) | 18.54(18.25) |
| O | CF$_3$ | CH$_3$ | CH$_2$CO$_2$C$_2$H$_5$ | C$_{18}$H$_{19}$F$_3$N$_2$O$_4$ | 55 | 136–138 | Cyclohexane | 474(390) | 56.35(56.25) | 4.89(4.98) | 7.19(7.29) | 15.00(14.83) |
| O | CF$_3$ | C$_6$H$_5$ | CH$_3$ | C$_{20}$H$_{17}$F$_3$N$_2$O$_2$ | 23 | 146.5–147.5 | Cyclohexane | 479(395) | 64.42(64.16) | 4.72(4.58) | 7.34(7.48) | 15.40(15.23) |
| NH | CH$_3$ | H | CH$_3$ | C$_{14}$H$_{17}$N$_3$O[d] | 29 | 254–256 | C$_6$H$_6$ | 409(375) | 69.26(69.11) | 6.93(7.04) | 17.32(17.27) | — |
| NH | CH$_3$ | CH$_3$ | CH$_3$ | C$_{15}$H$_{19}$N$_3$O | 26 | 245–246 | C$_6$H$_6$ | 408(370) | 69.96(70.01) | 7.40(7.44) | 16.28(16.33) | — |
| NH | CF$_3$ | H | CH$_3$ | C$_{14}$H$_{14}$F$_3$N$_3$O | 86 | 232.5–233.5 | C$_6$H$_6$ | 440(390) | 56.55(56.56) | 4.68(4.75) | 14.05(14.14) | 18.77(19.17) |
| NH | CF$_3$ | CH$_3$ | CH$_3$ | C$_{15}$H$_{16}$F$_3$N$_3$O | 90 | 246–248 | C$_6$H$_6$ | 442(390) | 57.40(57.87) | 5.14(5.18) | 13.17(13.50) | — |
| NH | OH[e] | H | CH$_3$ | C$_{13}$H$_{15}$N$_3$O$_2$ | 85 | >300 | 30% ethanol | — | 63.58(63.66) | 6.06(6.16) | 16.92(17.13) | — |
| NH | OCH$_3$[f] | H | CH$_3$ | C$_{14}$H$_{17}$N$_3$O$_2$ | 49 | 246–247 | Acetone | 393(360) | 64.39(64.84) | 6.57(6.61) | 15.96(16.21) | — |

[a] For the reaction of the hydroxy or aminotetrahydronaphthyridine with the appropriate β-keto ester.
[b] Made from 2 (the compound of Example 9) and maleic acid in concentrated sulfuric acid at 120° for 1 hours.
[c] Recovered in low yield as a by-product in the preparation of the compound where R'' = CH$_2$CO$_2$C$_2$H$_5$.
[d] The picrate after recrystallization from ethanol melted 213°–214°. Found: N, 17.77; theory, 17.79.
[e] Equivalent amounts of diethyl malonate and 1 (The compound of Example 5) were heated with stirring in diphenyl ether at 170°–180° for 1 hour; then the temperature was slowly raised during 2.5 hours to 245°. The product, which separated in part from the hot solution, was recovered by diluting the cooled mixture with benzene, chilling filtering, and washing, first with cold benzene, then with hexane. Based on both the ir and the $^1$H nmr the compound exists mainly in the 3-methylene-4-keto form.
[f] Made by methylating the previous compound with dimethyl sulfate at 55°–60° in basic 33% ethanol.

The effect of kind and position of substituents on the fluorescence maximum is the same as that observed with other coumarin and quinolone dyes. The most pronounced influence on the chromophore is noted with changes in the substituents on the carbonyl-containing ring. When R' is the electron-withdrawing $CF_3$ group, the fluorescence is red-shifted approximately 50 nm with the azacoumarins and 30–35 nm with the azaquinolones compared to the corresponding compounds with $R'=CH_3$. An electron-donating group, such as $OCH_3$, causes a 15–20 nm blue-shift in the fluorescence maximum compared to the analogous methyl compound; even a methyl group produces a small blue-shift when compared with the compound in which $R'=H$. Changes in B influence only slightly the position of the fluorescence maximum. The fluorescence of the azaquinolone dyes is always blue-shifted 20–40 nm over that of the corresponding azacoumarins.

The lasing activity of the compound in which: $X=O$, $R=H$, $R'=CH_3$ and $R''CH_3$ was reported by the inventors, with R. L. Atkins, in 16 *Opt. Comm* 313 (1976). The untuned wavelength was 490 nm with 9.0 kw initial peak output power and 650 shots to 50% decline at 5 J energy input at 0.5 Hz. The high output power versus input energy here represents a very efficient dye. In tests leading to that paper, it was found that a dye having the formula

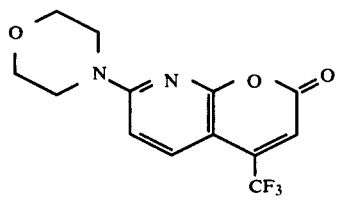

which has a chromophone similar to the dyes prepared by the methods set forth herein and summarized in the above table did not lase. Hence, that paper discloses the unpredictable nature of lasing behavior.

To prepare lasing solutions containing the compounds of this invention, the compounds may be dissolved in a solvent that does not absorb ultraviolet light in the region used to activate the compound or in the region that the dye is to lase. A representative but by no means comprehensive list of solvents includes water, alcohols suchs as methanol, ethanol and propanol, mixtures of such alcohols with water, benzene, toluene, mixtures of benzene and toluene, dimethyl formamide and dimethethy sulfoxide. To form a lasing solution, the dye is dissolved in the chosen solvent until the lowest energy absorption band, S'-S°, has an absorbance at its peak of 4 cm$^{-1}$(% transmission of 99.99 cm$^{-1}$).

What is claimed is:

1. The compounds having the structure:

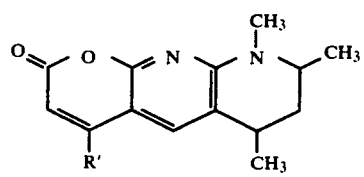

wherein R' is selected from the group consisting of H and $CH_3$.

2. The compounds having the structure:

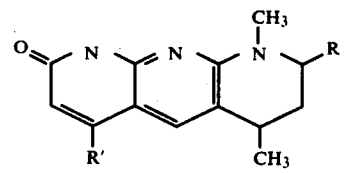

wherein R' is selected from the group consisting of $CH_3$, $CF_3$, OH and $OCH_3$ and wherein R is selected from the group consisting of H and $CH_3$.

3. The compounds having the structure:

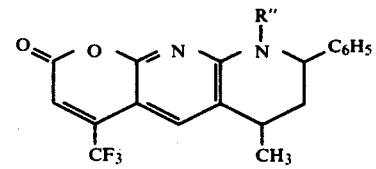

wherein R'' is selected from the group consisting of H, $CH_3$ and $CH_2CO_2C_2H_5$.

4. The compounds having the structure:

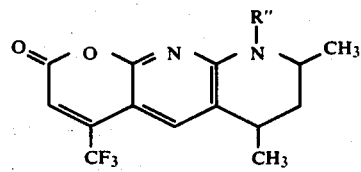

wherein R'' is selected from the group consisting of H and $CH_2CO_2C_2H_5$.

5. The compound having the structure:

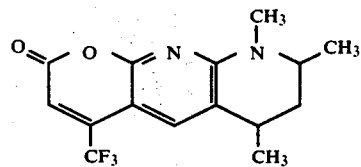

* * * * *